United States Patent
Martens et al.

(10) Patent No.: US 9,452,291 B2
(45) Date of Patent: Sep. 27, 2016

(54) DEVICE FOR PLANNING A NEUROMODULATION THERAPY

(71) Applicant: Medtronic Bakken Research Center B.V., Maastricht (NL)

(72) Inventors: Hubert Cécile Francois Martens, Eindhoven (NL); Michel Marcel José Decré, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 14/374,212

(22) PCT Filed: Jan. 22, 2013

(86) PCT No.: PCT/EP2013/051110
§ 371 (c)(1),
(2) Date: Jul. 23, 2014

(87) PCT Pub. No.: WO2013/110593
PCT Pub. Date: Aug. 1, 2013

(65) Prior Publication Data
US 2015/0045851 A1 Feb. 12, 2015

Related U.S. Application Data

(60) Provisional application No. 61/589,885, filed on Jan. 24, 2012.

(30) Foreign Application Priority Data

Jan. 24, 2012 (EP) .................................... 12152272

(51) Int. Cl.
*A61B 5/0476* (2006.01)
*A61B 5/055* (2006.01)
(Continued)

(52) U.S. Cl.
CPC ......... *A61N 1/36139* (2013.01); *A61B 5/0042* (2013.01); *A61B 5/055* (2013.01); *A61N1/36182* (2013.01); *A61N 1/37235* (2013.01); *A61N 1/37247* (2013.01); *G06F 17/5009* (2013.01); *G06F 19/3437* (2013.01); *A61N 1/37282* (2013.01)

(58) Field of Classification Search
USPC ........................................ 600/407, 410, 476
See application file for complete search history.

(56) References Cited

U.S. PATENT DOCUMENTS

2005/0070781 A1    3/2005  Dawant et al.
2005/0215884 A1*   9/2005  Greicius et al. .............. 600/410
(Continued)

FOREIGN PATENT DOCUMENTS

WO        2011159688 A2    12/2011

OTHER PUBLICATIONS

European Patent Office, International Search Report of PCT/US2013/020684, Apr. 3, 2013, WIPO, 4 pages.
(Continued)

*Primary Examiner* — Carl H Layno
*Assistant Examiner* — Jon Eric C Morales
(74) *Attorney, Agent, or Firm* — Shumaker & Sieffert, P.A.

(57) ABSTRACT

A device for planning a neuromodulation therapy, whereby the device comprises receiving means to receive brain default mode network data of a patient, template means comprising a template brain default mode network data, normalizing means being configured such that normalized patient brain default mode network data can be prepared on the basis on the received brain default mode network data and the template brain default mode network data, storage means comprising a brain default mode network database and comparison means configured such that the normalized patient brain default mode network data and the data contained in the brain default mode network database can be compared.

24 Claims, 2 Drawing Sheets

(51) Int. Cl.
  *A61B 5/05* (2006.01)
  *A61N 1/36* (2006.01)
  *A61B 5/00* (2006.01)
  *G06F 17/50* (2006.01)
  *G06F 19/00* (2011.01)
  *A61N 1/372* (2006.01)

(56) References Cited

U.S. PATENT DOCUMENTS

2005/0267347 A1 12/2005 Oster
2006/0017749 A1* 1/2006 McIntyre et al. ............ 345/664
2007/0203546 A1 8/2007 Stone et al.
2008/0081982 A1 4/2008 Simon et al.
2009/0292210 A1 11/2009 Culver et al.

OTHER PUBLICATIONS

Raichle, Marcus E., "The Brain's Dark Energy," Scientific American, Mar. 2010, pp. 44-49, 6 pages.
Liker et al., "Deep Brain Stimulation: An Evolving Technology", Proceedings of the IEEE, IEEE., vol. 96, No. 7, Jul. 1, 2008, pp. 1129-1141.

* cited by examiner

DEVICE FOR PLANNING A NEUROMODULATION THERAPY

CROSS REFERENCE TO RELATED APPLICATIONS

This application is an United States National Phase of International Patent Application PCT/EP2013/051110, entitled "Device for Planning A Neuromodulation Therapy," filed Jan. 22, 2013, which claims priority to European Patent Application No. 12 152 272.6, entitled "Device for Planning A Neuromodulation Therapy," filed Jan. 24, 2012, and claims priority to United States Provisional Application No. 61/589,885, entitled "Device for Planning A Neuromodulation Therapy," filed Jan. 24, 2012, the entire contents of each of which are hereby incorporated by reference in their entirety for all purposes.

TECHNICAL FIELD

The present invention relates to a device for planning a neuromodulation therapy.

BACKGROUND AND SUMMARY

The so-called "resting state" of a brain actually consists of a high level of activity and is estimated to account for approximately 95% of all brain energy consumption. A better terminology may be therefore the brain default mode network (DMN) which is believed to be the way that the brain organizes memory and prepares for future action (Raichle, M E, The Brain's Dark Energy, Scientific American, 2010). Disruptions to the DMN may underlie brain disorders like Alzheimer's, Parkinson's, depression, etc. Likewise, efficacious treatment of brain disorders possibly involves some level of restoration of DMN function.

New neuro-interventions are under development (i.e., neuromodulation therapies) that make use of brain-pacemakers, drug-delivery devices, or other implants to stimulate, activate, block or modulate certain neuronal targets in the brain with the purpose to reduce disease symptoms. The therapeutic mode of action of these novel therapies is usually a modification in neuronal network activity patterns leading to beneficial results. Such devices bear great promise to treat large patient groups who otherwise would receive sub-optimal therapies.

State-of-the-art targeting software uses anatomical patient images to determine the optimum site for neuromodulation therapy delivery. Sometimes this is augmented with local electrophysiological information for target-refinement. However, the therapeutic workings of neuromodulation devices are essentially occurring on a more global neuronal network level and this information cannot be captured by anatomical imaging and local electrophysiological exploration alone. For optimum treatment planning and execution, network aspects should be integrated.

It is therefore an object of the present invention to improve a device for planning a neuromodulation therapy, especially in that the device for planning a neuromodulation therapy is able to integrate network aspects to optimize treatment planning and execution of a neuromodulation therapy.

Accordingly, a device for planning a neuromodulation therapy comprises receiving means to receive brain default mode network data of a patient, template means comprising a template brain default mode network data, normalizing means being configured such that normalized patient brain default mode network data can be prepared on the basis on the received brain default mode network data and the template brain default mode network data, storage means comprising a brain default mode network database, and comparison means configured such that the normalized patient brain default mode network data and the data contained in the brain default mode network database can be compared.

By this, the advantage is achieved that network aspects can be integrated in the planning of the neuromodulation therapy and thus treatment planning and execution of a neuromodulation therapy can be improved.

Such a device may make use of a DMN database, e.g. an age-controlled healthy DMN, pathological DMN like Alzheimer's, Parkinson, depression, etc. to diagnose a patient's particular DMN and to couple this to an optimum neuromodulation treatment strategy. This coupling may be as simple as a look-up table that relates a DMN-diagnosis to one or more particular neuromodulation strategies, but it may also consist of a more advanced module in which DMN changes during various neuromodulation strategies are simulated and from which results a best outcome is selected automatically or manually by a user, i.e. by a physician.

Especially, the neuromodulation therapy may be a deep brain stimulation (DBS) therapy, i.e. an effective and accepted treatment involving the implantation of a "brain pacemaker", which sends mild electrical impulses to specific parts of the brain.

In a preferred embodiment the comparison means may be configured such that, based on the spatially normalized patient brain default mode network data and the data contained in the brain default mode network database, a DMN deviation map of the patient can be prepared and based on this DMN deviation map a pathology classification can be done, e.g., by a physician.

In a further preferred embodiment it is possible that the device comprises enhancement means comprising receiving means to receive anatomical data of the patient, preferably magnetic resonance data or magnetic resonance imaging data, and transferring means configured such that the anatomical data can be transferred to the normalizing means. By this, the advantage is achieved that the accuracy of the planning of the neuromodulation therapy can be enhanced due to the fact that the brain default mode network data of a patient and the template brain default mode network data are augmented by the anatomical data of the patient. Consequently, more data and information about the patient and the actual situation are available and thus a better planning result is possible.

Additionally, the device may further comprise mapping means configured such that a brain default mode network deviation map for the patient can be provided, whereby the deviation map preferably comprises a pathology classification.

It is possible that the device further comprises planning means configured such that at least one implant position for a neuromodulation therapy, preferably a deep brain stimulation therapy, can be planned. Exemplarily, based on the comparison of the spatially normalized patient brain default mode network data and the data contained in the brain default mode network database the optimal therapy targets can be identified and thereby also an identification of implant positions for electrodes for a neuromodulation therapy can be identified. It is commonly accepted that implant positions should be planned beforehand and also with high accuracy to achieve a good basis for the implant procedure itself. Based on a sufficient planning of the implant position, an implant may be implanted with high accuracy.

Thus, especially by the planning means the advantage is achieved that e.g. the implant position of a probe of a neuromodulation system can be planned with highest possible accuracy and thereby the basis is made for an accurate implantation of the probe, which is the further basis for a high accurate neuromodulation therapy.

Further preferably, the device further comprises simulation means configured such that at least one implant position can be chosen and its effects can be simulated. Thereby, the advantage is achieved that e.g. based on the planned implant position(s) the effects of a neuromodulation conducted by the implanted probes can be simulated and thus the efficiency and the accuracy of the neuromodulation can be checked. Advantageously, the effects of the planned neuromodulation can be tested and also e.g. unwanted side-effects can be detected and eliminated.

In a further preferred embodiment it is possible that the device further comprises display means configured such that the comparison conducted by the comparison means can be displayed. The display means may be e.g. a display on which the DMN deviation map of the patient and/or the planning of the implant positions and/or the simulation results can be displayed. The display means can also comprise a touch screen.

Furthermore, the device may comprise input means for inputting data and/or outputting means for outputting data. The input means can e.g. comprise a normal keyboard and/or touch screen and the output data can e.g. comprise beside any display means sound outputting means, preferably at least a loudspeaker.

Additionally, it is possible that the device comprises at least a workstation, whereby on the workstation at least one of the receiving means, the template means, the normalizing means, the brain default mode network database, the comparison means, the enhancement means, the mapping means, the planning means, and/or the simulation means is installed.

Furthermore, it is possible that the normalizing means are configured such that spatially normalized patient brain default mode network data can be prepared on the basis on the received brain default mode network data and/or that the normalized patient brain default mode network data are spatially normalized patient brain default mode network data.

Moreover, it is possible the device comprises checking and/or fine-tuning means configured such that brain default mode network data of a patient a neuromodulation therapy can be checked and/or used to fine-tune the planned neuromodulation program. Thereby, the advantage is achieved that in the post-operative phase real brain default mode network data of a patient can be used to check and fine-tune the planned neuromodulation therapy, which is preferably a deep brain stimulation therapy. E.g., brain default mode network data of a patient with one or more active implants for conducting the neuromodulation therapy can be used to assess the real effects and to conduct a fine-tuning of the neuromodulation therapy by, e.g., adjusting the therapy parameters if necessary.

BRIEF DESCRIPTION OF THE FIGURES

Further details and advantages of the present invention shall be described hereinafter with respect to the drawings.

DETAILED DESCRIPTION

Figure 1:
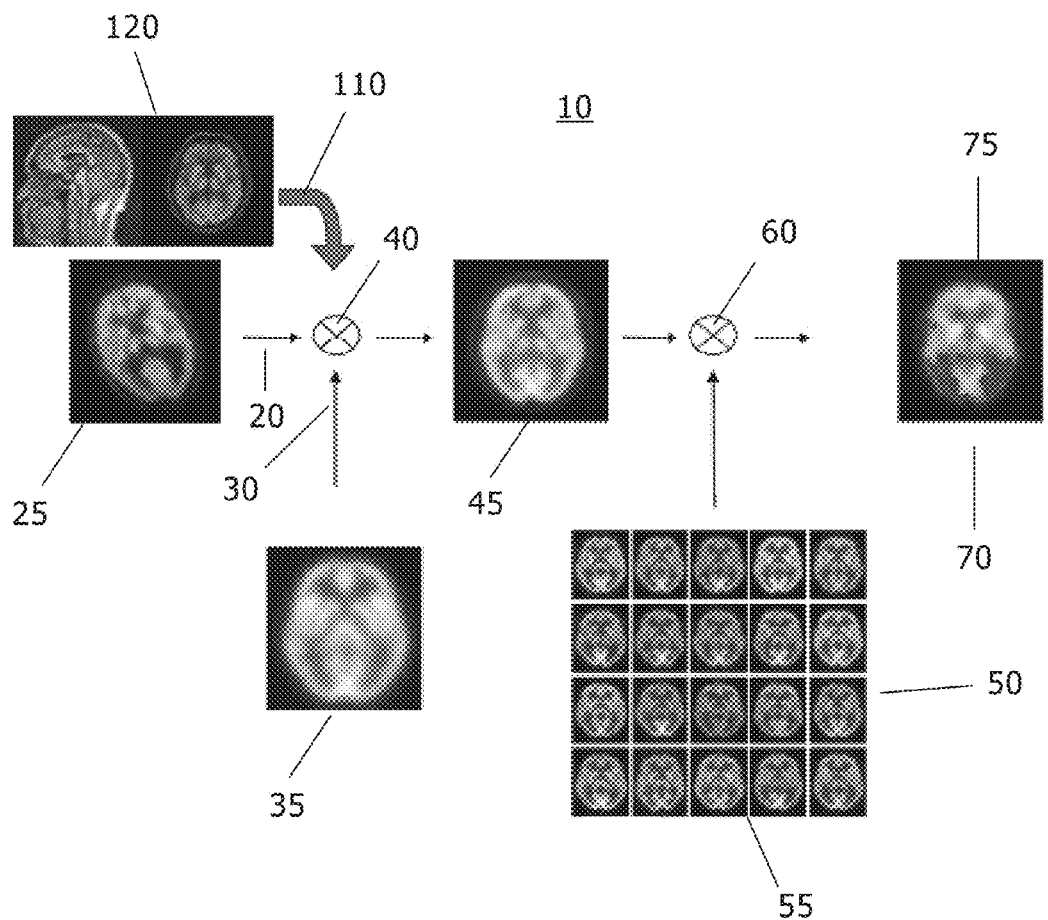
FIG. 1 shows a schematic overview of the DMN pathology classification conducted with/by the device for planning a neuromodulation therapy according to the present invention.

FIG. 1 shows a schematic overview of the DMN pathology classification conducted with/by the device 10 for planning a neuromodulation therapy according to the present invention.

The device 10 for planning a neuromodulation therapy comprises a workstation configured to receive patient DMN data (e.g., in the form of resting-state fMRI data or PET data, or network analysis of such fMRI, e.g., a dynamic causal modelling (DCM) analysis of fMRI data). As an option, DMN data may be registered to patient anatomical images to enhance spatial accuracy and/or couple DMN data to underlying anatomical structures.

The device 10 comprises receiving means 20 to receive brain default mode network data of a patient 25. The receiving means 20 may be embodied as an interface, which is configured such that the brain default mode network data of a patient 25 can be received and then processed by the device 10. The brain default mode network data of a patient 25 may be raw DMN data of a patient.

In the embodiment shown in FIG. 1, the raw DMN data of a patient are in the form of resting-state fMRI data or PET data, or network analysis of such fMRI, e.g., a dynamic causal modelling (DCM) analysis of fMRI data. As an option, DMN data may be registered to patient anatomical images to enhance spatial accuracy and/or couple DMN data to underlying anatomical structures so that one or more so-called DMN images of a patient can be obtained and used for the further processing.

Furthermore, the device 10 comprises template means 30 with at least one set of template brain default mode network data 35.

To enhance the planning procedure conducted with the device 10, the device comprises enhancement means 110. The enhancement means 110 comprise receiving means to receive anatomical data of the patient 120. In the preferred embodiment shown in FIG. 1, the anatomical data of the patient 120 are MR data, i.e., magnetic resonance imaging data of the brain of the patient. Additionally, the enhancement means 110 comprise transferring means configured such that the anatomical data 120 can be transferred to the normalizing means 40.

With the normalizing means 40, the spatially normalized patient brain default mode network data 45 can be prepared on the basis of the received brain default mode network data 25 and the template brain default mode network data 35.

The storage means 50 comprise at least one brain default mode network database 55. From this database 55 a classification of the patient DMN data may be obtained, for example a list of hyper/hypo-active regions for the particular patient or a DMN pattern-based disease classification or a set of model parameters that can be used for mathematically describing the patient's DMN (deviations) in a DMN computational model.

By means of the comparison means 60 the spatially normalized patient brain default mode network data 45 and the data contained in the brain default mode network database 55 are compared.

Based on this comparison the mapping means 70 of the device 10 generate a brain default mode network deviation map 75 for the patient, whereby the deviation map preferably comprises a pathology classification. This deviation map 75 can be displayed with a display of the device 10. This display can be a touch screen, which is connected to the workstation of the device 10 and which is not shown in detail in the drawings. Furthermore, the workstation can be connected with suitable input means such as a keyboard, a mouse, etc.

The DMN analysis is subsequently used to determine an optimum neuromodulation treatment. For example a list of hyper/hypo-active regions may be used to look up an optimum stimulation target by knowing the anatomical connections amongst various regions and selecting an optimal modulation target. Alternatively, a DMN model can be used to computationally test various neuromodulation strategies and then select the strategy that leads to maximal restoration of DMN activity towards standard levels/patterns.

Figure 2:
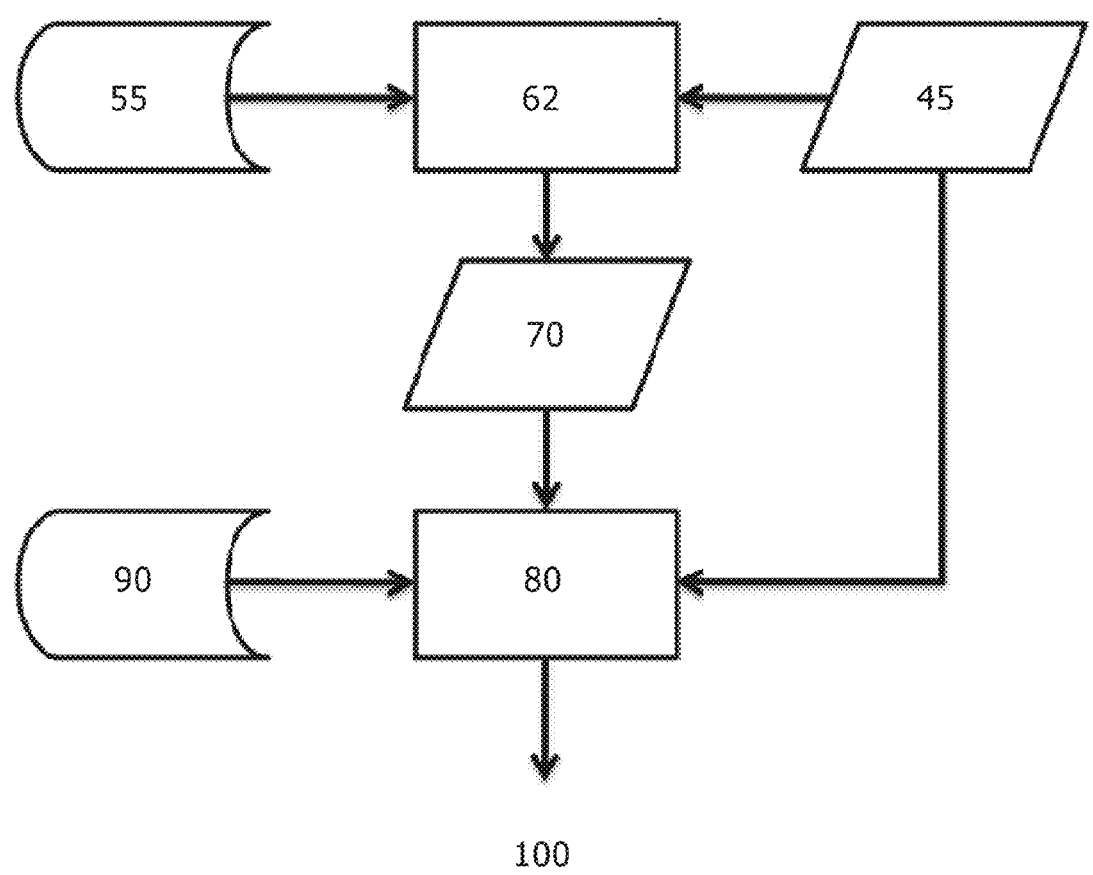
FIG. 2 shows a flowchart of the planning steps conducted with/by the device for planning a neuromodulation therapy according to the present invention.

FIG. 2 shows a flowchart of the planning steps conducted with/by the device 10 for planning a neuromodulation therapy according to the present invention.

Thereby, as a so-called first step of a pattern comparison 62 is conducted based on the patient DMN data 45, i.e., the spatially normalized patient brain default mode network data 45 and the data from the brain default mode network database 55, which has been described above and is shown in detail in FIG. 1.

Thereafter, the pathology classification is conducted and as described above brain default mode network deviation map 75 for the patient can be generated by the mapping means 70 of the device 10. Based on the pathology classification together with patient DMN data 45 and together with data from a neuromodulation database 90 therapy targets and a stimulation strategy 100 is generated.

The generation of the therapy targets and a stimulation strategy 100 is conducted by the planning means and simulation means, which are not shown in detail in the drawing and which are preferably embodied as a combined planning and simulation module.

With the planning means of the combined planning and simulation module at least one implant position for a neuromodulation therapy, here a deep brain stimulation therapy, can be planned. Exemplarily, based on the comparison of the spatially normalized patient brain default mode network data and the data contained in the brain default mode network database the optimal therapy targets can be identified and thereby also an identification of optimal implant positions for electrodes for a neuromodulation therapy can be identified.

With the simulation means of the combined planning and simulation module at least one implant position can be chosen and its effects can be simulated. Thereby, based on the planned implant position(s) the effects of a neuromodulation conducted by the implanted probes can be simulated and thus the efficiency and the accuracy of the neuromodulation can be checked. Additionally, the effects of the planned neuromodulation can be tested and also e.g. unwanted side-effects can be detected and eliminated.

The receiving means 20, the template means 30, the normalizing means 40, the brain default mode network database 55, the comparison means 60, the enhancement means 110, the mapping means 70, the planning means and/or the simulation means can comprise or may be at least partially embodied as one combined software module or several software modules that are interconnected. It is possible that such a software module or such software modules are directly installed on the workstation of the device 10. It is, however, also possible that the software module or such software modules are installed on a remote workstation, which is interconnected with the workstation of the device 10, e.g., by means of a network like the internet, a private network or a virtual private network.

Such a software module can be embodied as a computer program product.

It is however also possible that the means of the device 10, in particular the receiving means 20, the template means 30, the normalizing means 40, the brain default mode network database 55, the comparison means 60, the enhancement means 110, the mapping means 70, the planning means, and/or the simulation means are at least partially embodied as an electronic module, especially a microelectronic module.

It is moreover also preferably possible that the device 10 comprises checking and/or fine-tuning means configured such that for a brain default mode network data of a patient, a neuromodulation therapy can be checked and/or used to fine-tune the planned neuromodulation program.

The invention claimed is:

1. A computing device for planning a neuromodulation therapy, comprising:
   receiving means for receiving brain default mode network data of a patient;
   template means for generating a template brain default mode network data;
   normalizing means for preparing normalized patient brain default mode network data on the basis of the received brain default mode network data and the template brain default mode network data;
   storage means for storing a brain default mode network database;
   comparison means for comparing the normalized patient brain default mode network data and the data contained in the brain default mode network database;
   planning means for generating a plan defining at least one implant position for neuromodulation therapy based on the comparison; and
   outputting means for outputting an indication of the at least one implant position.

2. The device for planning a neuromodulation therapy according to claim 1, wherein the device comprises enhancement means for receiving anatomical data of the patient, the anatomical data augmenting the default mode network data.

3. The device for planning a neuromodulation therapy according to claim 2, wherein the device further comprises mapping means for providing a brain default mode network deviation map for the patient based on the normalized patent brain default mode network data and data contained in the brain default mode network database.

4. The device for planning a neuromodulation therapy according to claim 3, wherein the deviation map comprises a pathology classification.

5. The device for planning a neuromodulation therapy according to claim 2, wherein the anatomical data of the patient comprises one of magnetic resonance data or magnetic resonance imaging data.

6. The device for planning a neuromodulation therapy according to claim 2, wherein the enhancement means further comprises transferring means for transferring the anatomical data to the normalizing means.

7. The device for planning a neuromodulation therapy according to claim 1, wherein the device further comprises simulation means configured for simulating effects of the planned at least one implant position of the neuromodulation therapy.

8. The device for planning a neuromodulation therapy according to claim 7, wherein the device further comprises display means for displaying the comparison conducted by the comparison means.

9. The device for planning a neuromodulation therapy according to claim 7, wherein the device further comprises at least one of: an input means for inputting data or an outputting means for outputting data.

10. The device for planning a neuromodulation therapy according to claim 7, wherein the device further comprises a workstation, the workstation comprising at least one of the receiving means, the template means, the normalizing means, the brain default mode network database, the comparison means, the enhancement means, the mapping means, the planning means, or the simulation means.

11. The device for planning a neuromodulation therapy according to claim 1, wherein the normalizing means are for preparing a spatially normalized patient brain default mode network data on the basis of the received brain default mode network data.

12. The device for planning a neuromodulation therapy according to claim 1, wherein the device comprises fine-tuning means for fine tuning a planned neuromodulation program based on received brain default mode network data of a patient.

13. The device for planning a neuromodulation therapy according to claim 1, wherein the neuromodulation therapy comprises a deep brain stimulation therapy.

14. The device for planning a neuromodulation therapy according to claim 1, wherein the normalizing means comprises means for spatially normalizing patient brain default mode network data.

15. A method comprising:
receiving, by a computing device, brain default mode network data of a patient;
generating, by the computing device, a template brain default mode network data;
preparing, by the computing device, normalized patient brain default mode network data on the basis of the received brain default mode network data and the template brain default mode network data;
comparing, by the computing device, the normalized patient brain default mode network data to data contained in a brain default mode network database;
generating, by the computing device, a plan defining at least one implant position for neuromodulation therapy based on the comparison; and
outputting, by the computing device, an indication of the at least one implant position.

16. The method of claim 15, further comprising:
providing a default mode network deviation map for the patient based on the normalized patient brain default mode network data and data contained in the brain default mode network database.

17. The method of claim 15, further comprising:
simulating an effect of the planned at least one implant position of the neuromodulation therapy.

18. The method of claim 15, further comprising:
displaying the comparison of the normalized patient brain default mode network data to data contained in a brain default mode network database.

19. The method of claim 15, wherein preparing normalized patient brain default mode network data further comprises:
preparing a spatially normalized patient brain default mode network data on the basis of the received brain default mode network data.

20. A device for planning a neuromodulation therapy comprising:
a computing device configured to:
receive brain default mode network data of a patient;
generate a template brain default mode network data;
prepare normalized patient brain default mode network data on the basis of the received brain default mode network data and the template brain default mode network data;
compare the normalized patient brain default mode network data to data contained in a brain default mode network database;
generate a plan defining at least one implant position for neuromodulation therapy based on the comparison; and
output an indication of the at least one implant position.

21. The device of claim 20, wherein the computing device is further configured to provide a default mode network deviation map for the patient based on the normalized patient brain default mode network data and data contained in the brain default mode network database.

22. The device of claim 20, wherein the computing device is further configured to simulate an effect of the planned at least one implant position of the neuromodulation therapy.

23. The device of claim 20, wherein the computing device if further configured to generate a display of the comparison of the normalized patient brain default mode network data to data contained in a brain default mode network database.

24. The device of claim 20, wherein preparing normalized patient brain default mode network data further comprises:
preparing a spatially normalized patient brain default mode network data on the basis of the received brain default mode network data.

* * * * *